United States Patent
Bly et al.

(10) Patent No.: US 8,244,378 B2
(45) Date of Patent: Aug. 14, 2012

(54) SPIRAL CONFIGURATIONS FOR INTRAVASCULAR LEAD STABILITY

(75) Inventors: Mark J. Bly, Falcon Heights, MN (US); Randy W. Westlund, River Falls, WI (US); Ronald W. Heil, Jr., Roseville, MN (US); Brendan E. Koop, Coon Rapids, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 658 days.

(21) Appl. No.: 11/668,926

(22) Filed: Jan. 30, 2007

(65) Prior Publication Data

US 2008/0183259 A1   Jul. 31, 2008

(51) Int. Cl.
*A61N 1/00* (2006.01)
(52) U.S. Cl. ......... 607/127; 607/115; 607/116; 607/131
(58) Field of Classification Search .................. 607/115, 607/127, 131
See application file for complete search history.

(56) References Cited

U.S. PATENT DOCUMENTS

| | | |
|---|---|---|
| 4,365,634 A | 12/1982 | Bare et al. |
| 4,414,986 A | 11/1983 | Dickhudt et al. |
| 4,774,949 A | 10/1988 | Fogarty |
| 4,905,667 A | 3/1990 | Foerster et al. |
| 4,920,979 A | 5/1990 | Bullara |
| 4,944,088 A | 7/1990 | Doan et al. |
| 5,016,808 A | 5/1991 | Heil, Jr. et al. |
| 5,221,261 A | 6/1993 | Termin et al. |
| 5,265,608 A | 11/1993 | Lee et al. |
| 5,330,515 A | 7/1994 | Rutecki et al. |
| 5,351,394 A * | 10/1994 | Weinberg ......................... 29/872 |
| 5,354,318 A | 10/1994 | Taepke |
| 5,378,239 A | 1/1995 | Termin et al. |
| 5,383,922 A | 1/1995 | Zipes et al. |
| 5,387,233 A | 2/1995 | Alferness et al. |
| 5,411,546 A | 5/1995 | Bowald et al. |
| 5,423,865 A * | 6/1995 | Bowald et al. ..................... 607/5 |
| 5,476,498 A | 12/1995 | Ayers |
| 5,496,277 A | 3/1996 | Termin et al. |
| 5,531,779 A | 7/1996 | Dahl et al. |
| 5,540,730 A | 7/1996 | Terry, Jr. et al. |
| 5,639,276 A | 6/1997 | Weinstock et al. |
| 5,755,714 A | 5/1998 | Murphy-Chutorian |
| 5,755,761 A | 5/1998 | Obino |
| 5,766,203 A | 6/1998 | Imran et al. |
| 5,772,693 A * | 6/1998 | Brownlee ..................... 607/123 |

(Continued)

FOREIGN PATENT DOCUMENTS

DE      10103288      8/2002

(Continued)

OTHER PUBLICATIONS

International Search Report and Written Opinion of international application No. PCT/US2007/086127, mailed Apr. 3, 2008, 15 pp.

(Continued)

*Primary Examiner* — Nicole F Lavert
(74) *Attorney, Agent, or Firm* — Faegre Baker Daniels LLP

(57) ABSTRACT

A medical electrical lead for transvascularly stimulating a nerve, muscle or other tissue from an adjacent vessel is described. The lead includes an expandable distal portion having one or more spirals for securing and stabilizing the lead within the vessel.

7 Claims, 11 Drawing Sheets

U.S. PATENT DOCUMENTS

| | | | |
|---|---|---|---|
| 5,792,187 | A | 8/1998 | Adams |
| 5,803,928 | A | 9/1998 | Tockman et al. |
| 5,871,531 | A | 2/1999 | Struble |
| 5,954,761 | A | 9/1999 | Machek et al. |
| 5,997,536 | A | 12/1999 | Osswald et al. |
| 6,006,134 | A | 12/1999 | Hill et al. |
| 6,021,354 | A | 2/2000 | Warman et al. |
| 6,055,456 | A | 4/2000 | Gerber |
| 6,292,695 | B1 | 9/2001 | Webster, Jr. et al. |
| 6,321,123 | B1 | 11/2001 | Morris et al. |
| 6,363,288 | B1 | 3/2002 | Bush et al. |
| 6,385,492 | B1 | 5/2002 | Ollivier et al. |
| 6,397,109 | B1 | 5/2002 | Cammilli et al. |
| 6,429,217 | B1 | 8/2002 | Puskas |
| 6,442,413 | B1 | 8/2002 | Silver |
| 6,449,507 | B1 | 9/2002 | Hill et al. |
| 6,516,232 | B2 | 2/2003 | Skinner |
| 6,564,096 | B2 | 5/2003 | Mest |
| 6,584,362 | B1 | 6/2003 | Scheiner et al. |
| 6,600,956 | B2 | 7/2003 | Maschino et al. |
| 6,656,960 | B2 | 12/2003 | Puskas |
| 6,671,562 | B2 | 12/2003 | Osypka et al. |
| 6,704,604 | B2 | 3/2004 | Soukup et al. |
| 6,760,626 | B1 | 7/2004 | Boveja |
| 6,766,203 | B2 | 7/2004 | Doan et al. |
| 6,778,854 | B2 | 8/2004 | Puskas |
| RE38,654 | E | 11/2004 | Hill et al. |
| RE38,705 | E | 2/2005 | Hill et al. |
| 6,882,887 | B1 * | 4/2005 | Shelchuk et al. ............ 607/122 |
| 6,889,092 | B2 | 5/2005 | Zhu et al. |
| 6,901,297 | B2 | 5/2005 | Fericks et al. |
| 6,934,583 | B2 | 8/2005 | Weinberg et al. |
| 6,934,589 | B2 | 8/2005 | Sundquist et al. |
| 6,973,340 | B2 | 12/2005 | Fuimaono et al. |
| 7,047,084 | B2 | 5/2006 | Erickson et al. |
| 7,058,454 | B1 | 6/2006 | Chitre et al. |
| 7,215,896 | B2 | 5/2007 | Yamada et al. |
| 7,676,275 | B1 | 3/2010 | Farazi et al. |
| 7,917,230 | B2 | 3/2011 | Bly |
| 7,949,409 | B2 | 5/2011 | Bly et al. |
| 2002/0026228 | A1 | 2/2002 | Schauerte |
| 2002/0029030 | A1 | 3/2002 | Lurie et al. |
| 2002/0032963 | A1 | 3/2002 | Lindegren |
| 2002/0087192 | A1 | 7/2002 | Barrett et al. |
| 2002/0151949 | A1 * | 10/2002 | Dahl et al. ............... 607/126 |
| 2002/0183237 | A1 | 12/2002 | Puskas |
| 2002/0183817 | A1 | 12/2002 | Van Venrooij et al. |
| 2002/0198570 | A1 | 12/2002 | Puskas |
| 2002/0198571 | A1 | 12/2002 | Puskas |
| 2003/0074039 | A1 | 4/2003 | Puskas |
| 2003/0078623 | A1 | 4/2003 | Weinberg et al. |
| 2003/0105506 | A1 | 6/2003 | Krishnan et al. |
| 2003/0195506 | A1 | 10/2003 | Stewart et al. |
| 2003/0195603 | A1 * | 10/2003 | Scheiner et al. ............ 607/122 |
| 2003/0199961 | A1 | 10/2003 | Bjorklund et al. |
| 2003/0229380 | A1 | 12/2003 | Adams et al. |
| 2004/0015151 | A1 | 1/2004 | Chambers |
| 2004/0015204 | A1 | 1/2004 | Whitehurst et al. |
| 2004/0015205 | A1 | 1/2004 | Whitehurst et al. |
| 2004/0019359 | A1 | 1/2004 | Worley et al. |
| 2004/0019377 | A1 | 1/2004 | Taylor et al. |
| 2004/0030362 | A1 | 2/2004 | Hill et al. |
| 2004/0059383 | A1 | 3/2004 | Puskas |
| 2004/0059404 | A1 | 3/2004 | Bjorklund et al. |
| 2004/0062852 | A1 | 4/2004 | Schroeder et al. |
| 2004/0133240 | A1 | 7/2004 | Adams et al. |
| 2004/0147825 | A1 | 7/2004 | Milojevic et al. |
| 2004/0172075 | A1 | 9/2004 | Shafer et al. |
| 2004/0172088 | A1 | 9/2004 | Knudson et al. |
| 2004/0176782 | A1 | 9/2004 | Hanse et al. |
| 2004/0186531 | A1 | 9/2004 | Jahns et al. |
| 2004/0260374 | A1 | 12/2004 | Zhang et al. |
| 2005/0021119 | A1 | 1/2005 | Sage et al. |
| 2005/0038489 | A1 | 2/2005 | Grill |
| 2005/0060015 | A1 | 3/2005 | Tanaka |
| 2005/0065553 | A1 | 3/2005 | Ezra et al. |
| 2005/0080472 | A1 | 4/2005 | Atkinson et al. |
| 2005/0113862 | A1 | 5/2005 | Besselink et al. |
| 2005/0131467 | A1 | 6/2005 | Boveja |
| 2005/0143412 | A1 | 6/2005 | Puskas |
| 2005/0149126 | A1 | 7/2005 | Libbus |
| 2005/0149155 | A1 | 7/2005 | Scheiner et al. |
| 2005/0197675 | A1 | 9/2005 | David et al. |
| 2005/0251239 | A1 | 11/2005 | Wallace et al. |
| 2006/0206153 | A1 | 9/2006 | Libbus et al. |
| 2006/0229677 | A1 | 10/2006 | Moffitt et al. |
| 2006/0241737 | A1 | 10/2006 | Tockman et al. |
| 2006/0259085 | A1 | 11/2006 | Zhang et al. |
| 2006/0259107 | A1 | 11/2006 | Caparso et al. |
| 2008/0051861 | A1 | 2/2008 | Cross et al. |
| 2008/0183186 | A1 | 7/2008 | Bly et al. |
| 2008/0183187 | A1 | 7/2008 | Bly |
| 2008/0183253 | A1 | 7/2008 | Bly |
| 2008/0183254 | A1 | 7/2008 | Bly et al. |
| 2008/0183255 | A1 | 7/2008 | Bly et al. |
| 2008/0183264 | A1 | 7/2008 | Bly et al. |
| 2008/0183265 | A1 | 7/2008 | Bly et al. |
| 2009/0171425 | A1 | 7/2009 | Dahlberg |
| 2011/0152877 | A1 | 6/2011 | Bly |

FOREIGN PATENT DOCUMENTS

| | | |
|---|---|---|
| EP | 045317 | 10/1991 |
| EP | 0453117 | 10/1991 |
| EP | 0795343 | 9/1997 |
| EP | 1208867 | 5/2002 |
| EP | 1304135 | 4/2003 |
| JP | 05049701 A | 3/1993 |
| WO | 8304181 | 12/1983 |
| WO | 9956817 | 11/1999 |
| WO | WO 9955412 | 11/1999 |
| WO | 0100273 A1 | 1/2001 |
| WO | 0218006 | 3/2002 |
| WO | 2006098996 | 9/2006 |
| WO | WO 2006110338 | 10/2006 |

OTHER PUBLICATIONS

Nabutovsky et al., "Lead Design and Initial Applications of a New Lead for Long-Term Endovascular Vagal Stimulation," PACE, vol. 30, Jan. 2007 Supplement 1, pp. S215-S218.

Web Site, Guidant Fineline II Sterox and Fineline II Sterox EZ, http://www.guidant.com/productstemplates/crm/fineline_II_sterox.shtml.

Tarver et al., "Clinical Experience with a Helical Bipolar Stimulating Lead," PACE, Oct., Part II 1992, pp. 1545-1556, vol. 15, Cyberonics, Inc., Webster, Texas and the Department of Neurosurgery, Baylor College of Medicine.

Li et al, "Vagal Nerve Stimulation Markedly Improves Long-Term Survival After Chronic Heart Failure in Rats," Circulation Journal of the American Heart Association, Dec. 8, 2003, pp. 120-124.

International Search Report and Written Opinion of international application No. PCT/US2008/051700, mailed Jun. 25, 2008, 13 pages.

International Search Report and Written Opinion of international application No. PCT/US2007/086130, mailed Apr. 9, 2008, 15 pages.

International Search Report and Written Opinion of international application No. PCT/US2007/086118, mailed May 21, 2008, 14 pages.

International Search Report and Written Opinion of international application No. PCT/US2007/086119, mailed Apr. 3, 2007, 15 pages.

International Search Report and Written Opinion of international application No. PCT/US2007/086120, mailed Apr. 14, 2008, 14 pages.

International Search Report and Written Opinion of international application No. PCT/US2007/086124, mailed Apr. 8, 2008, 14 pages.

International Search Report and Written Opinion of international application No. PCT/US2007/086125, mailed Apr. 9, 2008.

* cited by examiner

SPIRAL CONFIGURATIONS FOR INTRAVASCULAR LEAD STABILITY

CROSS-REFERENCE TO RELATED APPLICATIONS

This application is related to the following co-owned applications: DUAL SPIRAL LEAD CONFIGURATIONS, filed on Jan. 30, 2007, and assigned Ser. No. 11/668,887, now published application no. US 2008/0183254; ELECTRODE CONFIGURATIONS FOR TRANSVASCULAR NERVE STIMULATION, filed Jan. 30, 2007, and assigned Ser. No. 11/668,957, now published application no. US 2008/0183264; TRANSVASCULAR LEAD WITH PROXIMAL FORCE RELIEF, filed on Jan. 30, 2007, and assigned Ser. No. 11/669,039, now published application no. US 2008/0183265; METHOD AND APPARATUS FOR DELIVERING A TRANSVASCULAR LEAD, filed on Jan. 30, 2007, and assigned Ser. No. 11/669,042, now published application no. US 2008/0183186; DIRECT DELIVERY SYSTEM FOR TRANSVASCULAR LEAD, filed on Jan. 30, 2007 and assigned Ser. No. 11/669,047, now published application no. US 2008/0183187; SIDE PORT LEAD DELIVERY SYSTEM, filed on Jan. 30, 2007, and assigned Ser. No. 11/669,050, now published application no. US 2008/0183255; and NEUROSTIMULATING LEAD HAVING A STENT-LIKE ANCHOR, filed on Jan. 30, 2007, and assigned Ser. No. 11/668,834, now published application no. US 2008/0183253, all of which are herein incorporated by reference.

TECHNICAL FIELD

The present invention relates to medical electrical leads for nerve or muscle stimulation and their configurations. More specifically, the present invention relates to medical electrical lead configurations for stabilizing leads in an intravascular location adjacent a nerve to be stimulated.

BACKGROUND

A significant amount of research has been directed both to the direct and indirect stimulation of nerves including the left and right vagus nerves, the sympathetic and parasympathetic nerves, the phrenic nerve, the sacral nerve, and the cavernous nerve to treat a wide variety of medical, psychiatric, and neurological disorders or conditions. More recently, stimulation of the vagus nerve has been proposed as a method for treating various heart conditions, including heart failure.

Typically in the past, nerve stimulating electrodes were cuffs placed in direct contact with the nerve to be stimulated. A much less invasive approach is to stimulate the nerve through an adjacent vein using an intravascular lead. A lead including one or more electrodes is inserted into a patient's vasculature and delivered to a site within a vessel adjacent a nerve to be stimulated. However, without any additional means of stabilizing the lead within the vein, the lead can move and/or rotate causing the electrodes to migrate from the stimulation site.

Thus, it is desirable to develop a mechanism for minimizing lead rotation and movement and allow for chronic therapy to be reliably delivered.

SUMMARY

According to one embodiment, the present invention is a medical electrical lead for stimulating a nerve. The lead is adapted to be delivered to a stimulation site within a vessel adjacent to the nerve to be stimulated and includes: a proximal end adapted to be connected to a pulse generator; a lead body including an expandable distal portion for securing and stabilizing the lead at a stimulation site; and one or more electrodes located on the distal portion. The distal portion includes a first spiral, a second spiral, and a straight portion occurring between the first and second spirals. The spirals have a predetermined effective diameter and are configured to expand and frictionally engage at least one vessel wall. One or more electrodes located on the distal portion are adapted to deliver an electrical pulse transvascularly to the nerve. When the distal portion expands, at least one electrode is placed in close proximity to the nerve to be stimulated.

According to another embodiment, the present invention is a medical electrical lead for stimulating a nerve. The lead is adapted to be delivered to a stimulation site within a vessel adjacent to the nerve to be stimulated and includes: a proximal end adapted to be connected to a pulse generator; a lead body including an expandable distal portion for securing and stabilizing the lead at the stimulation site; and one or more electrodes located on the distal portion. The distal portion includes at least one spiral having a predetermined effective diameter, wherein the spiral is configured to expand and frictionally engage at least one vessel wall. One or more electrodes located on the distal portion are adapted to deliver an electrical pulse transvascularly to the nerve. When the distal portion expands, at least one electrode is placed in close proximity to the nerve to be stimulated.

According to yet another embodiment, the present invention is a method for stimulating a nerve or muscle from an adjacent vessel using an intravascular medical electrical lead including an expandable distal portion having one or more spirals for securing and stabilizing the lead at the stimulation site. The method includes: collapsing the distal portion; delivering the distal portion of the lead to a stimulation site located within an adjacent vessel to the nerve; and stimulating the adjacent nerve. The lead is connected to a pulse generator and includes one or more electrodes located on the distal portion. At least one electrode is adapted to deliver an electrical pulse transvascularly to the nerve or muscle to be stimulated.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
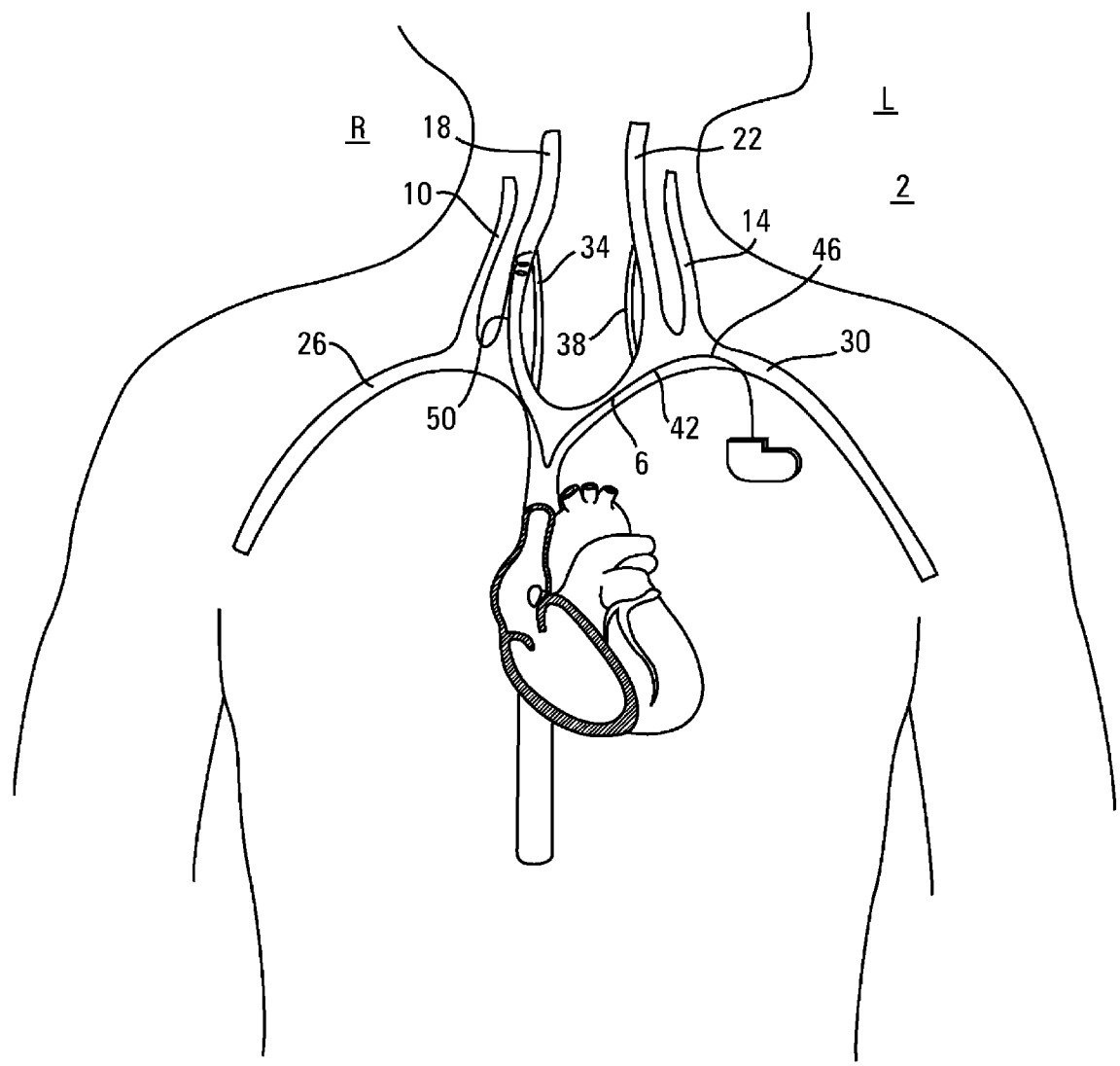
FIG. 1 is a schematic drawing of a lead deployed in a patient's internal jugular vein at a location adjacent the vagus nerve according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

While the embodiments described herein generally refer to placement of a lead into the right internal jugular vein through the left or right subclavian vein, the various embodiments of the present invention as described below can be practiced at numerous sites within a patient's vasculature system. Any intravascular site that is adjacent to a nerve, muscle, or brain tissue that has the potential to benefit from stimulation is a potential site for stimulation. The term "vessel" includes all veins and arteries of the circulatory system. Additionally, the term "vessel" includes various structures of the lymphatic system, including lymph nodes, ducts, capillaries, and vessels. Likewise, as used herein, the term "vessel" also includes the various tube-like structures of the gastrointestinal system. The terms "nerve" and "nerve fiber" as used herein include a single neuron, nerve, nerve ending(s), or nerve bundle. The term "intravascular" means within the venous or arterial circulatory system, including vessels of all types and descriptions. When referring to "intravascular stimulation" in describing the embodiments of the present invention, it is meant to refer to stimulation from within the circulatory system resulting in (transvascular) stimulation of a nerve, muscle, or tissue of interest. The term "transvascular" means across a vessel or vessel wall. "Stimulation" means a stimulus, usually electrical, which causes depolarization of a cell or cells, or portion of a cell, contraction, excitation as measured by, e.g., calcium or sodium influx into the cell, or an altered membrane potential across a cell.

Vessels of sufficient diameter for catheter access which are known to have nerves running adjacent to or nearby are suitable candidates for potential stimulation sites. Exemplary sites include, but are not limited to, the following: the left and right internal jugular veins, the azygous vein, the brachiocephalic (innominate) vein, the subclavian vein, the superior vena cava, the pulmonary artery, and cardiac branch vessels. Other potential stimulation sites include, but are not limited to, the following: the thoracic duct, the bile duct, and sites along the upper gastrointestinal and lower gastrointestinal tracts. Exemplary nerves to be stimulated include, but are not limited to, the following: the left and right vagus nerves, the phrenic nerve, the parasympathetic nerves, the sympathetic nerves, and the sacral nerve.

Figure 2:
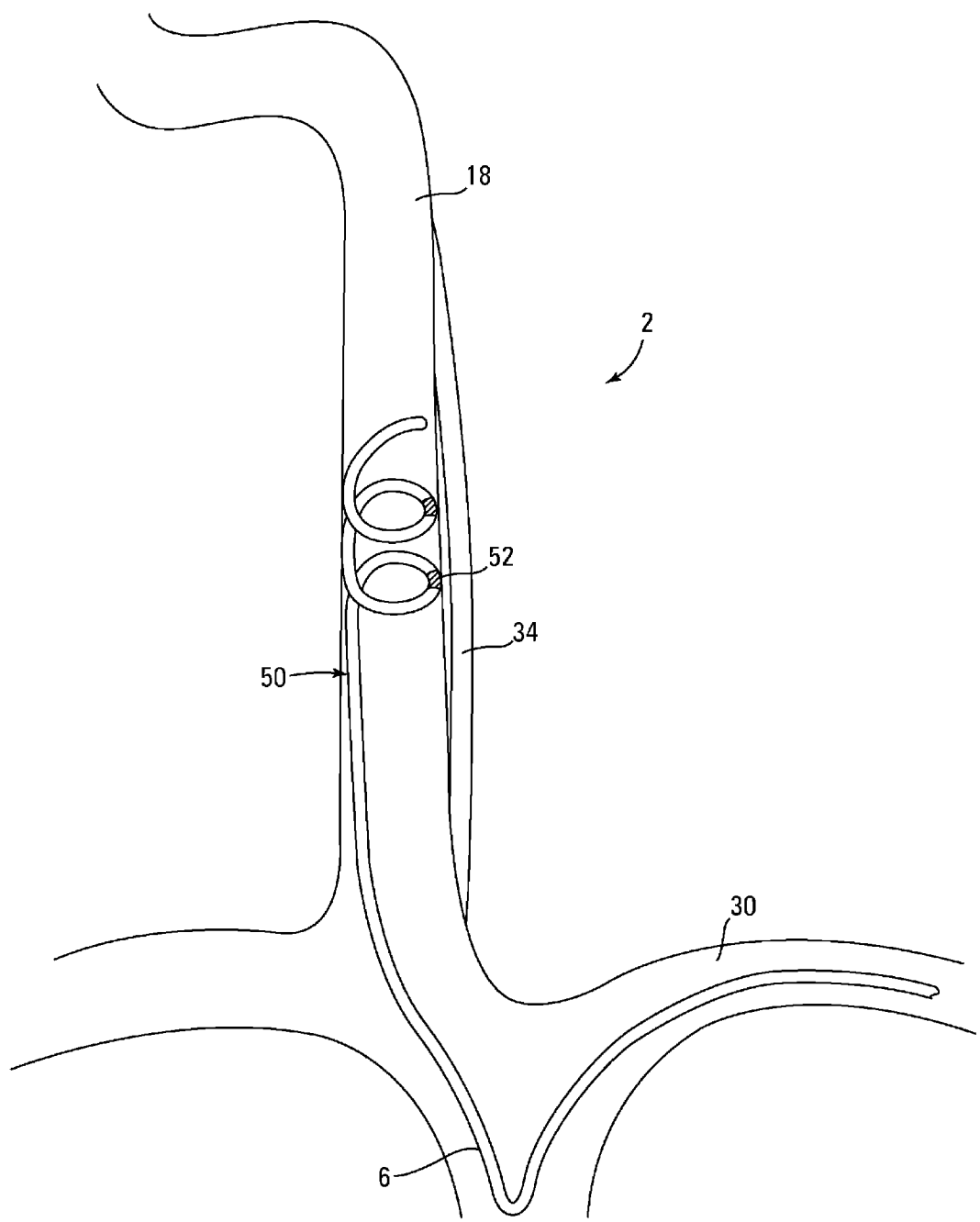
FIG. 2 is a close-up, schematic view of a lead deployed in a patient's internal jugular vein as shown in FIG. 1 according to an embodiment of the present invention.
Figure 3:
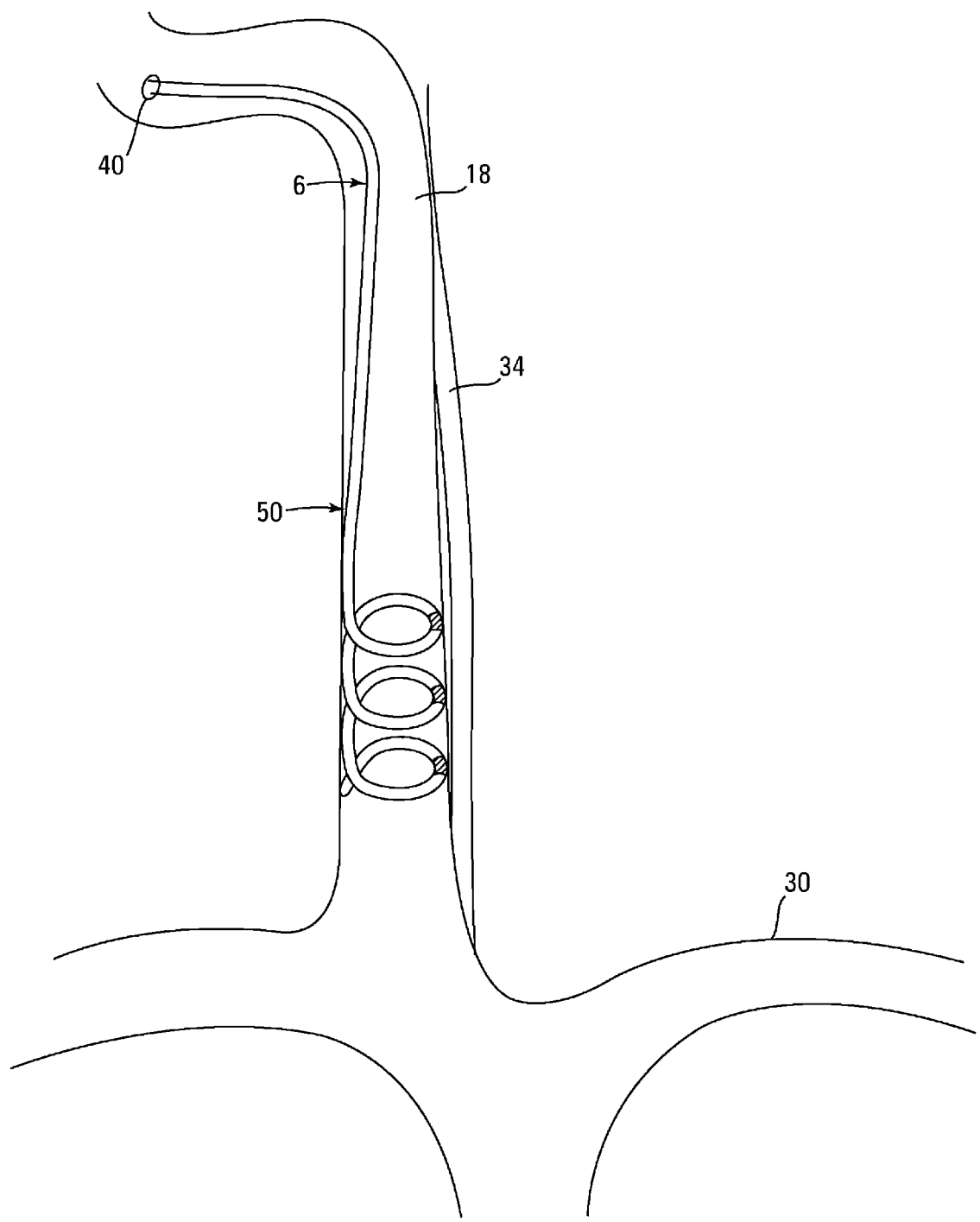
FIG. 3 is a schematic view of a lead deployed in a patient's internal jugular vein inserted through a superior access site according to another embodiment of the present invention.

FIG. 1 shows a perspective view of a patient's vascular system 2 showing a lead 6 deployed within the system 2. FIG. 2 is an exploded view of the lead 6 deployed within the system 2. In general, the vascular system 2, as shown, includes the right and left external jugular veins 10 and 14, the right and left internal jugular veins 18 and 22, the right and left subclavian veins 26 and 30, portions of which are generally aligned with the right and left vagus nerves 34 and 38. As shown in FIGS. 1 and 2, a lead 6 is inserted into a patient's vasculature system through the left subclavian vein 30 and into the right internal jugular vein 18. According to one embodiment, as shown in FIG. 3, the lead 6 can be inserted via percutaneous stick through a superior site 40 in the internal jugular vein 18. Alternatively, the lead 6 can be inserted via percutaneous stick from an inferior site. Finally, the lead 6 can be inserted and advanced into the vasculature system using a same side approach via the right subclavian vein 26. The lead 6 is positioned in the right internal jugular vein 18 adjacent to the right vagus nerve 34.

Figure 4:
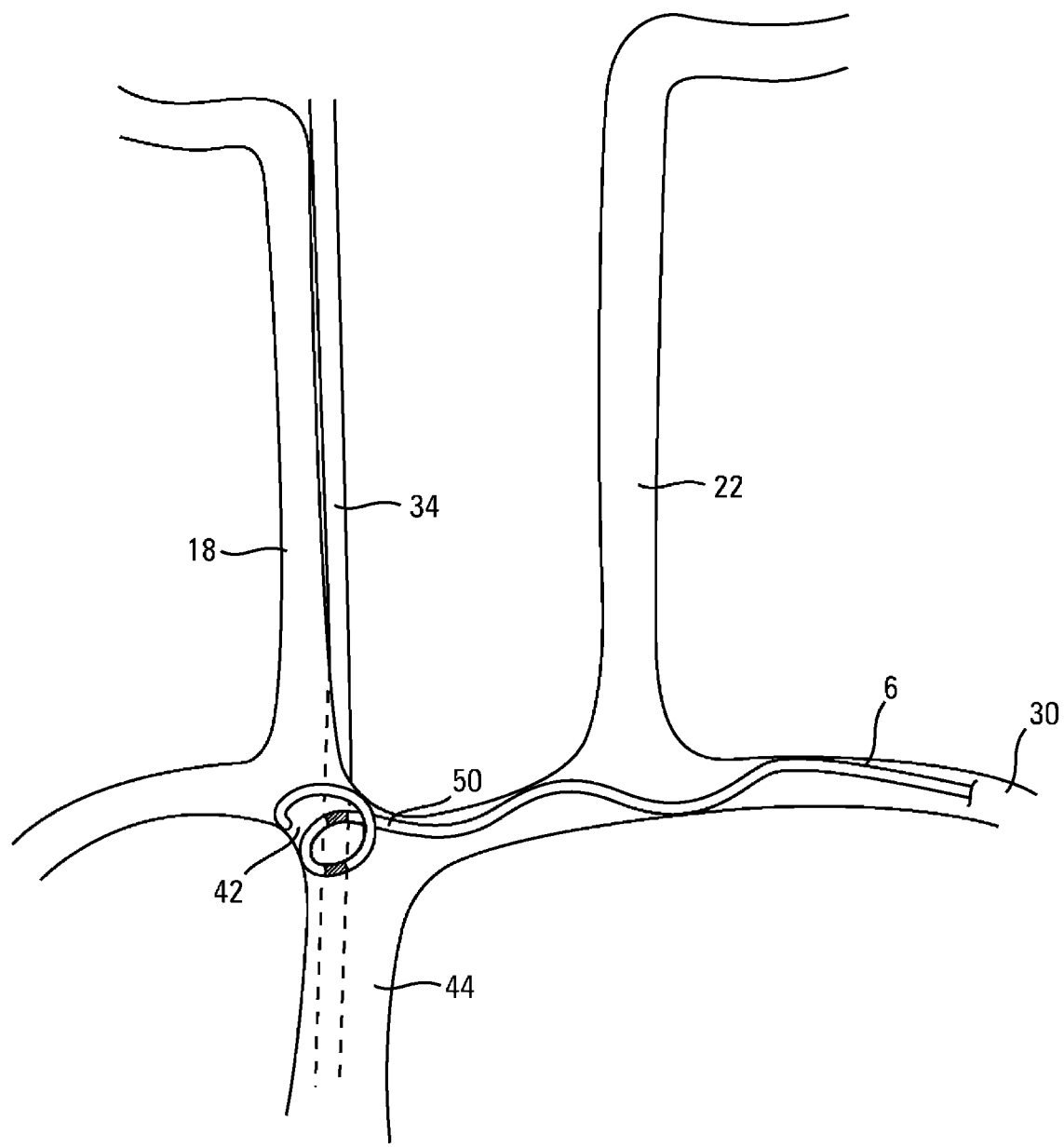
FIG. 4 is a schematic view of a lead deployed in a patient's brachiocephalic vein according to another embodiment of the present invention.
Figure 5:
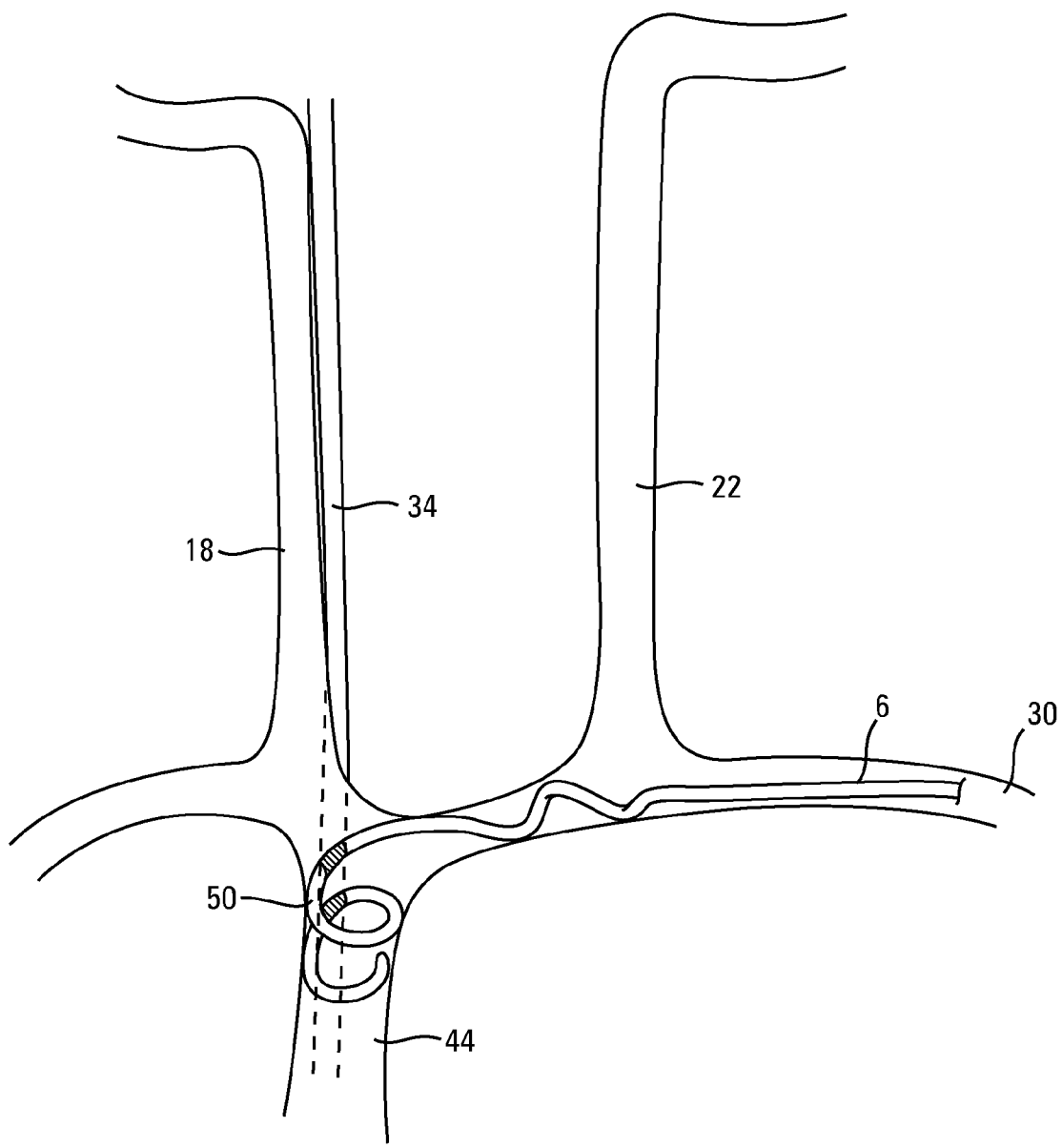
FIG. 5 is a schematic view of a lead deployed in a patient's superior vena cava according to another embodiment of the present invention.

FIGS. 4 and 5 show the lead 6, according to embodiments of the present invention, deployed within alternative locations in a patient's vasculature for stimulating the vagus nerve 34. According to one embodiment, as shown in FIG. 4, the lead 6 is inserted through the left subclavian vein 30 and deployed within the brachiocephalic vein 43. The portion of the vagus nerve 34 adjacent to the brachiocephalic vein 43 is represented by the dashed lines in FIG. 4. According to another embodiment, as shown in FIG. 5, the lead 6 is inserted through the left subclavian vein 30 and deployed and secured in the superior vena cava 44. The portion of the vagus nerve 34 adjacent to the superior vena cava 44 is represented by the dashed lines in FIG. 5.

Figure 6:
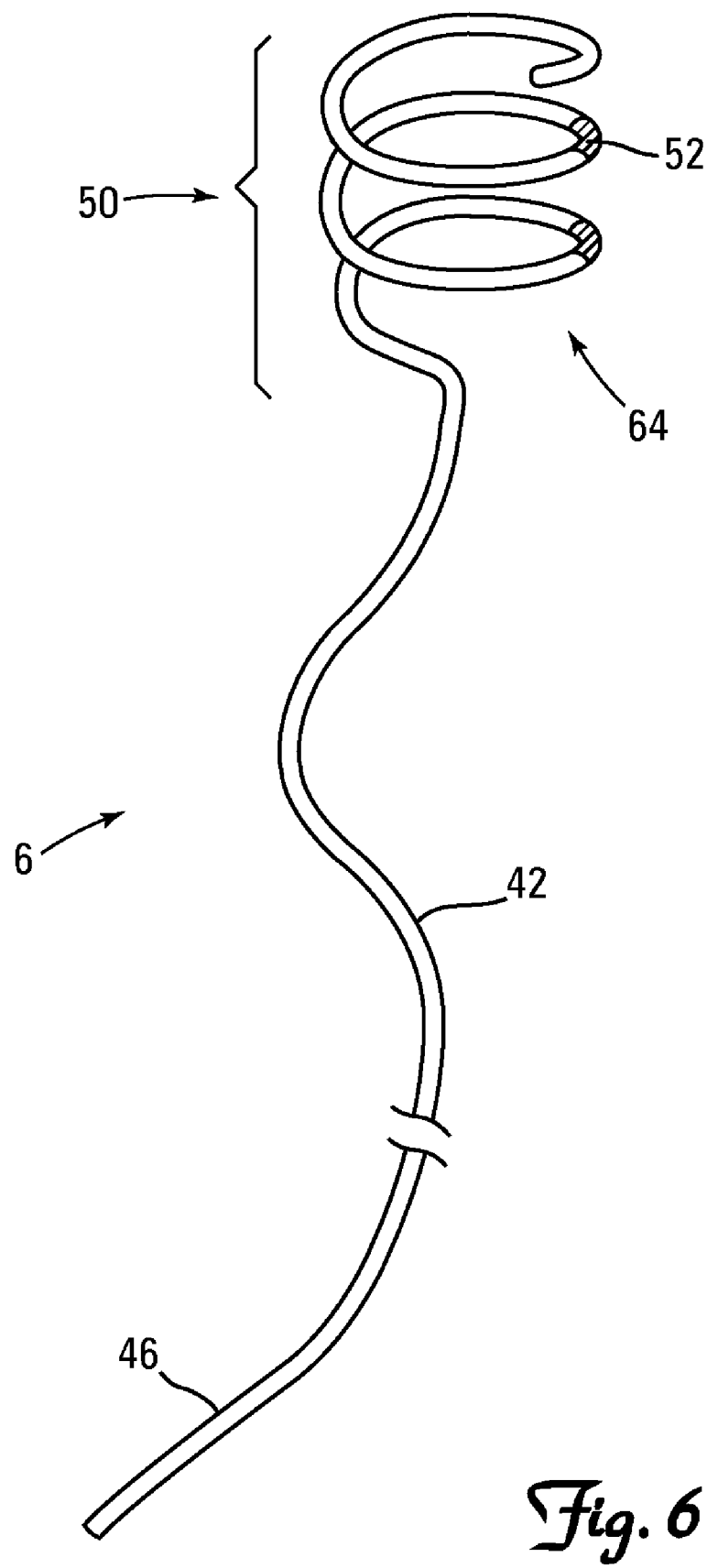
FIG. 6 is a perspective view of a lead according to an embodiment of the present invention.

FIG. 6 is a perspective view of a lead 6 according to an embodiment of the present invention. As shown in FIG. 6, the lead 6 includes a lead body 42 including a proximal portion 46 and a distal portion 50 including one or more electrodes 52. Additionally, the lead 6 includes a proximal end adapted to be connected to a pulse generator or other implantable medical device. The lead body 42 is flexible, but substantially non-compressible along its length, and has a circular cross-section.

According to one embodiment of the present invention, the lead body 42 includes a plurality of conductors. The conductors can be wires, coils, cables or combinations thereof. The plurality of conductors includes individual wires. These wires can be insulated conductive wires, coils, or cables and/or molded in place with an insulator such as silicone, polyurethane, ethylene tetrafluoroethylene, or another biocompatible, insulative polymer. Alternatively, according to another embodiment of the present invention, the lead body 42 has a co-radial design. In this embodiment, each individual conductor is separately insulated using tubing or the like, and then wound together in parallel to form a single coil. Alternatively, the lead body 42 is co-axial. According to a further embodiment of the present invention, each conductor is adapted to connect to an individual electrode 52 in a one-to-one manner allowing each electrode 52 to be individually addressable. In yet a further embodiment of the present invention, the lead body 42 includes a lumen adapted to receive a guiding element such as a guidewire or a stylet for collapsing (partially or fully) and guiding the distal portion 50 of the lead to a stimulation site within a vessel. Finally, the lead body 42 may have any configuration as is known in the art.

According to another embodiment of the present invention, the distal portion 50 is stiffer than the lead body 42 including the proximal portion 46. One exemplary embodiment of such a structure is disclosed in commonly assigned and co-pending published Application No. US 2008/0183265, entitled "Transvascular Lead With Proximal Force Relief," which is herein incorporated by reference.

Additionally, the distal portion 50 is adapted to transition between a collapsed configuration adapted for insertion of the lead 6 through a patient's vasculature system and an expanded configuration adapted to secure and stabilize the distal portion 50 of the lead 6 in a vessel. A guiding element such as a guide catheter or a guidewire is adapted to be inserted into the distal portion 50 such that the distal portion 50 collapses and can be advanced through the vasculature system to the target stimulation site.

According to one embodiment of the present invention, the distal portion 50 includes a superelastic material. Exemplary superelastic materials include Nitinol and MP35N.

Figure 7A:
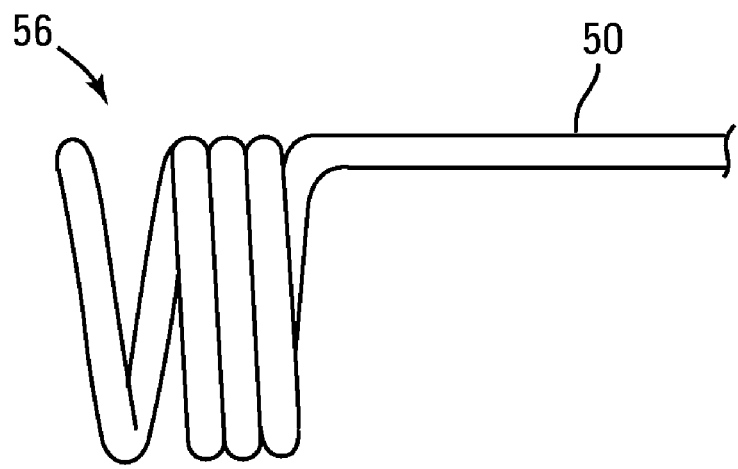
FIGS. 7A-7B show side views of a distal portion of a lead according to various embodiments of the present invention.
Figure 7B:
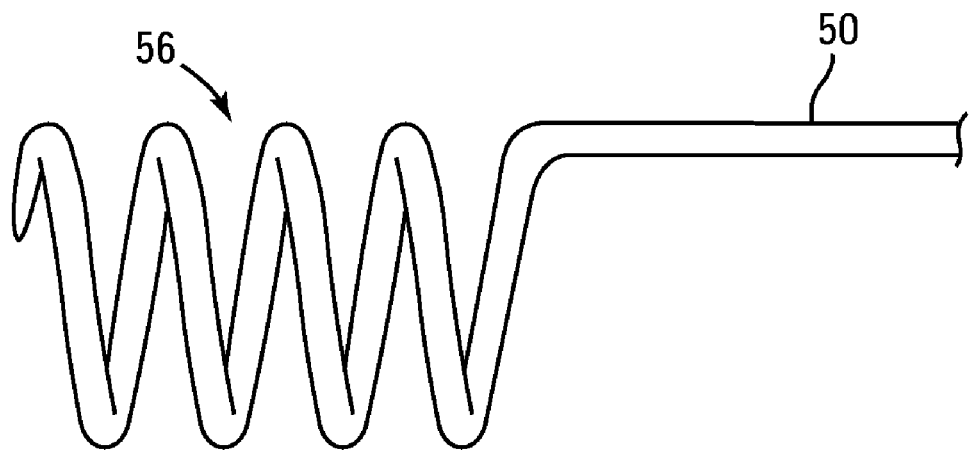

As best viewed in FIGS. 7A-7B, the distal portion 50 of the lead 6 includes one or more helical turns forming a spiral 64. The turns of the spiral 64 can wind in a clockwise or counter-clockwise direction. The number of turns can range from a ½ turn to multiple turns. The pitch can be described as the distance between two points on a spiral. The pitch can vary along the spiral 64, ranging from zero centimeters (lasso configuration) to 5 cm, or can remain constant. Additionally, the spiral 64 has a predetermined, effective outer diameter. The effective outer diameter of the spiral 64 is selected such that it is slightly greater than the inner diameter of the vessel in which it is deployed. According to one embodiment of the present invention, the effective outer diameter of the spiral 64 ranges from 5 to about 50 mm. According to another embodiment of the present invention, the effective outer diameter of the spiral 64 ranges from about 10 to about 35 mm. Additionally, the spiral 64 can assume a variety of cross-sectional shapes. According to one embodiment, the spiral 64 has a circular cross-sectional shape. A circular cross-sectional shape allows no bias for orientation such that when the lead is rotated within a vein the spiral 64 exhibits no natural preference for a specific orientation. According to another embodiment, the spiral 64 has an elliptical cross-sectional shape. The overall size, diameter and cross-sectional shape of the spiral 64 can be selected depending upon the size, diameter, and shape of the vessels in which the distal portion 50 of the lead 6 is to be deployed. An overall length of a spiral 64, according to an embodiment of the present invention, ranges from about 30 mm to about 200 mm depending on the anatomical demands of the patient's anatomy. More particularly, an overall length of the spiral 64 ranges from about 40 mm to about 80 mm.

According to a further embodiment of the present invention the spiral 64 can increase in diameter from a proximal end of the spiral to a distal end of the spiral creating a spiral 64 having a predetermined shape that tapers down from a distal end of the spiral 64 to a proximal end of the spiral 64. Alternatively, the spiral 64 can have a diameter that decreases from a proximal end of the spiral 64 to a distal end of the spiral 64, creating a spiral 64 having a predetermined shape that tapers down from a proximal end of the spiral 64 towards the distal end of the spiral 64.

Figure 8:
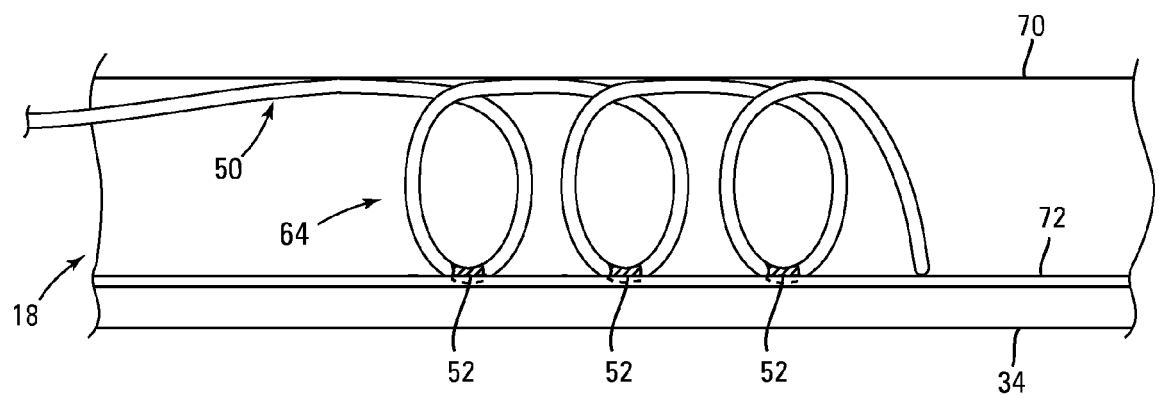
FIG. 8 is a close-up, schematic view of a distal portion of a lead deployed in a vessel according to an embodiment of the present invention.

FIG. 8 is a close-up schematic view of a distal portion 50 of a lead 6 deployed within the right internal jugular vein 18 adjacent the right vagus nerve 34. Upon deployment in a patient's vasculature, the spiral 64 is configured to radially expand such that it contacts and frictionally engages an inner surface of the vessel walls 72, 74, securing and stabilizing the distal portion 50 of the lead 6 at a stimulation site within the vessel. The stimulation site can be described as the location within a vessel adjacent a nerve or muscle which maximizes electrical stimulation to the nerve or muscle across the vessel walls. According to an embodiment of the present invention, the spiral 64 places enough lateral force on the vessel walls 72, 74 without damage such that the spiral 64 migrates outside of the vessel wall 72, 74 towards the nerve 34 to be stimulated. As a result, any electrodes 52 located on the spiral 64 are placed in close proximity to the nerve 34. In one exemplary embodiment, the electrode 52 is disposed at a distance of less than 2 mm from the nerve 34 to be stimulated. In another exemplary embodiment of the present invention, the spiral 64 forces the vessel wall 72, 74 into direct contact with the nerve 34.

The spiral 64 is adapted to transition from a collapsed configuration to an expanded configuration. In its expanded configuration, the spiral 64 has a predetermined effective diameter and is adapted to frictionally engage at least one wall of the vessel in which the distal portion 50 is deployed. According to one embodiment of the present invention, when allowed to expand within a vessel, the spiral 64 will not achieve its predetermined effective diameter as the spiral 64 will be constrained from fully expanding by the walls of the vessel in which it is deployed. As such the spiral 64 places a radial expansion force on the walls of the vessel, providing a mechanism for stabilizing the distal portion 50 of the lead 6 in the vessel. In one exemplary embodiment, the effective outer diameter ranges from about 5 percent to about 50 percent greater than the inner diameter of the vessel in which the distal portion 50 of the lead 6 is disposed.

According to an embodiment of the present invention, the lead body can include a lumen adapted to receive a guiding element such as a stylet or a guidewire adapted to assist in delivery of the distal portion 50 to a stimulation site within a vessel. Alternatively, a guide catheter is provided to deliver the distal portion 50 to a stimulation site within a vessel. The stylet, guidewire, or guide catheter, either alone or in combination with one another, is used to collapse (either fully or partially) the distal portion 50 including the spiral 64 from an expanded configuration to a collapsed configuration (full or partial) and also to guide the distal portion 50 of the lead through the patient's vasculature system. Once collapsed, the distal portion 50 can be inserted into a patient's vasculature and guided to a stimulation site within a vessel. When the stimulation site has been reached the guiding element is removed, allowing the distal portion 50 to transition from a collapsed configuration to an expanded configuration.

According to a further embodiment of the present invention, a guide catheter is used to deliver the distal portion 50 of the lead 6 to the stimulation site within a vessel. Once inside the targeted vessel, the distal portion can be partially deployed from the guide catheter and rotated or otherwise manipulated. The electrodes located on the distal portion can be used to acutely stimulate and thus, test, potential stimulation sites. Once a stimulation site has been selected using the information gained through acute stimulation, the guide catheter can be fully retracted and the distal portion deployed so as to secure and stabilize the distal portion at a stimulation site within the vessel such that stimulation can occur at the targeted stimulation site.

According to another embodiment of the present invention, the spiral 64 is variably expandable. That is, the spiral 64 is adapted to expand with and adapt to the natural changes in the size and diameter of the vessel while at the same time engaging and maintaining a frictional force on the vessel walls. For example, when in the internal jugular vein, the internal geometry (diameter and inner shape) of the internal jugular vein may change with blood flow and blood pressure. Similarly, when a patient is in an upright position, the diameter of the vessel may be smaller than when the patient is lying down or is in a prone position. The spiral 64 accounts for the difference in vessel diameter by expanding so as to maintain a frictional force on the vessel walls securing and stabilizing the distal portion 50 in the vessel.

According to another embodiment of the present invention, the distal portion 50 includes one or more electrodes 52 located on the spiral 64. At least one electrode 52 is adapted to deliver an electrical pulse transvascularly to the nerve or muscle to be stimulated. Additionally, according to another embodiment of the present invention, at least one electrode 52 can be a sensing electrode. At least one electrode 52 is oriented towards the nerve or muscle to be stimulated. In yet a further embodiment of the present invention, the circular cross-section of the spiral 64 allows for easy orientation of the electrodes 52 toward the adjacent nerve or muscle to be stimulated. Since a spiral having a circular cross-section has no particular preference for orientation, the spiral can be rotated or otherwise manipulated using such that the electrical stimulation across the vessel wall to the adjacent nerve is maximized. As the spiral 64 expands within a vessel, as shown in FIG. 8, the electrode(s) 52 is pushed up against the vessel walls 72, 74 maximizing transvascular stimulation of the vagus nerve 34. In one embodiment, the spiral 64 presses up against the vessel walls 72, 74 with enough lateral force such that the spiral 64 migrates outside the vessel wall bringing at least one electrode 52 in closer proximity to the adjacent nerve. More particularly, the spiral 64 places enough radial expansion force on the vessel walls 72, 74 such that the turns of the spiral 64 migrate outside of the original boundaries of the vessel walls 72, 74 and towards the nerve 34 to be stimulated without damaging the vessel walls 72, 74. As a result, any electrodes 52 located on the spirals 64 are placed in closer proximity to the nerve 34.

The migration of the spiral outside of the original boundaries of the vessel walls causes no damage to the vessel walls nor does the spiral erode through the vessel walls. A sheath of tissue forms over the spiral over an extended period of time such that it becomes encapsulated within the vessel walls. The outer geometry of the vessel is altered such that the outline of the spiral located within the vessel is visible.

Figure 9:
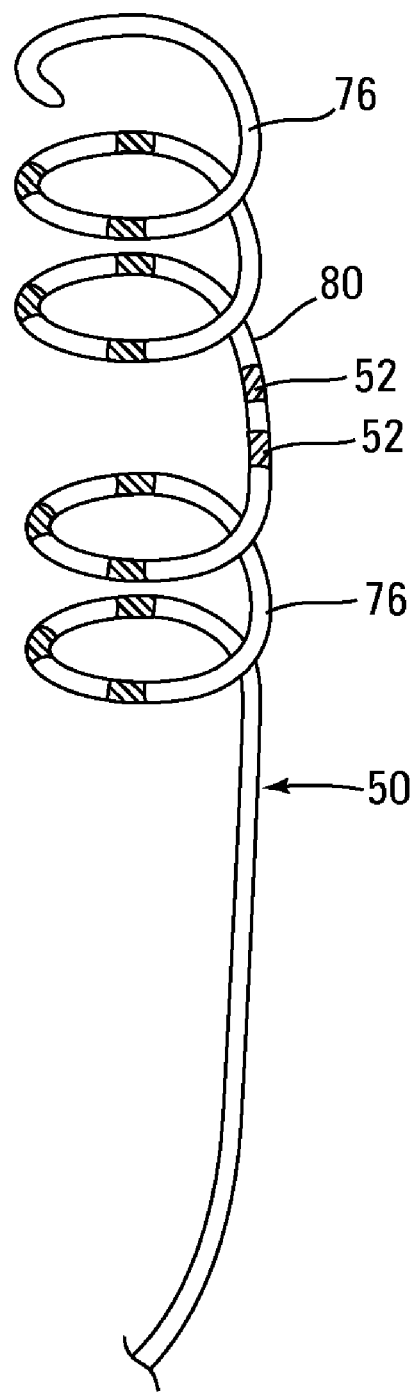
FIG. 9 is a side view of a distal portion of a lead according to an embodiment of the present invention.
Figure 10:
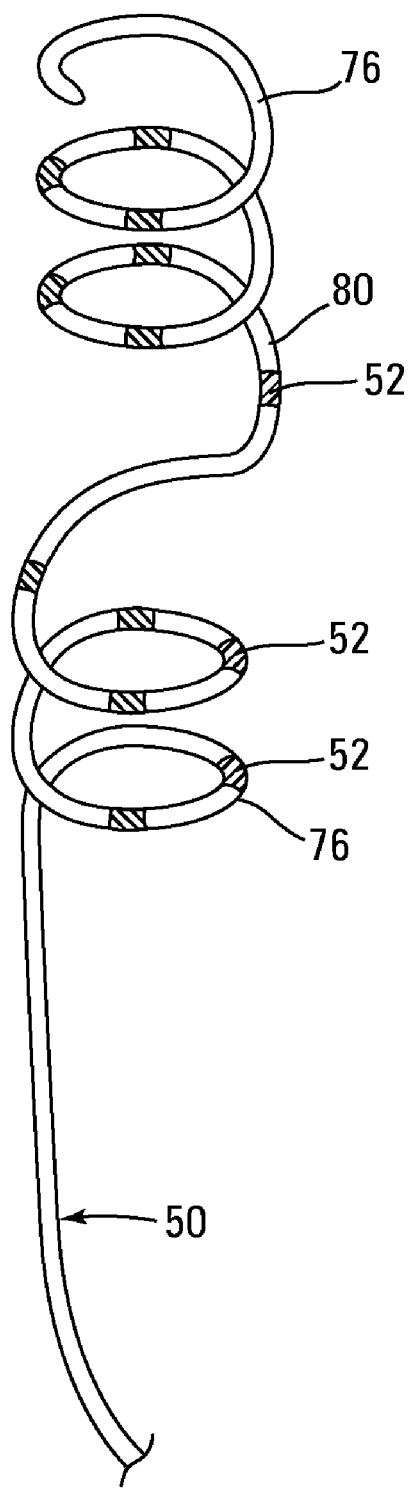
FIG. 10 is a side view of a distal portion of a lead according to another embodiment of the present invention.

According to another embodiment of the present invention, as shown in FIGS. 9-10, the distal portion 50 of the lead 6 includes one or more sets of helical turns forming one or more spirals 76. The helical turns of each spiral 76 can wind in the same direction, as shown in FIG. 9 or, alternatively, can wind in opposing directions, as shown in FIG. 10. According to a further embodiment of the present invention, the spirals 76 are interrupted by a generally straight portion 80 of the lead body 42. The generally straight portion 80 is configured such that it runs parallel to the nerve to be stimulated. Electrodes 52 may be located on one or both of the spirals 76, the straight portion 80, or a combination thereof.

Figure 11:
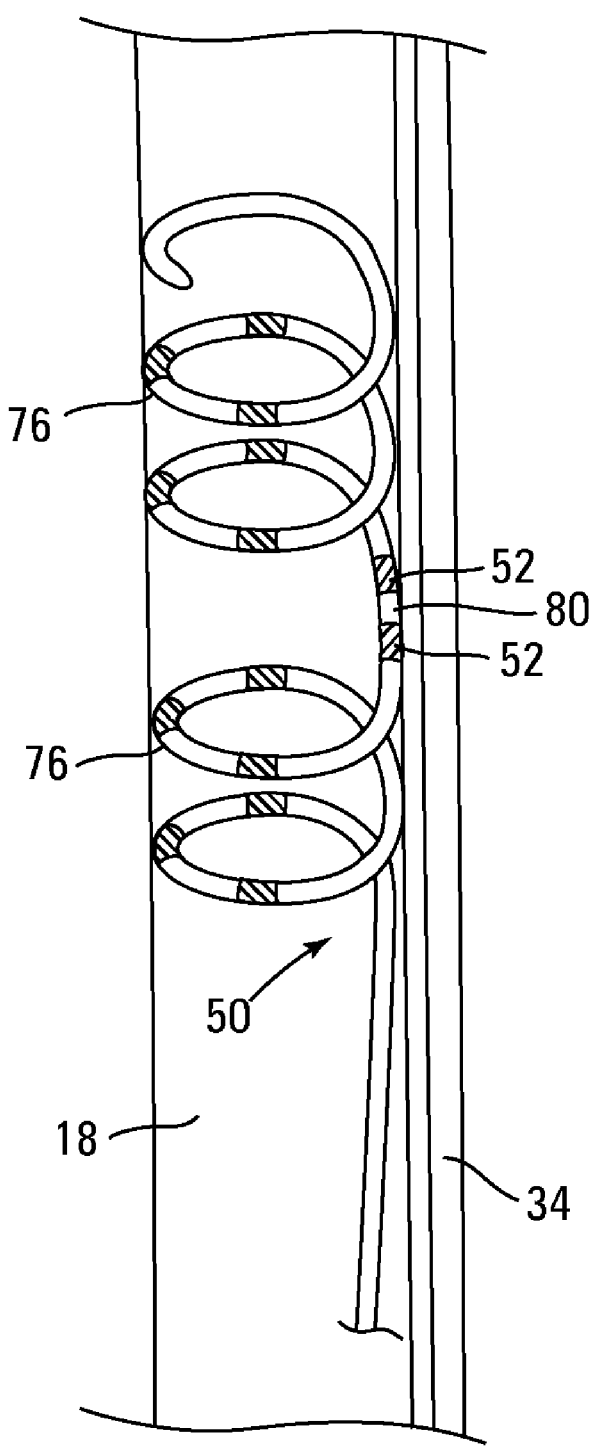
FIG. 11 is a close-up schematic view of a distal portion of a lead as shown in FIG. 9 deployed in a vessel according to an embodiment of the present invention.

FIG. 11 is a schematic view of a distal portion 50 of a lead 6 including one or more spirals 76 deployed in a vessel adjacent a nerve to be stimulated. According to an embodiment of the present invention, the electrodes 52 are located on a straight portion 80 of the lead body 42. The spirals 76 stabilize the distal portion 50 of the lead 6 and push the electrodes 52 up against the vessel wall in which the distal portion 50 of the lead 6 is deployed such that the electrodes 52 are in parallel alignment with and in close proximity to the adjacent nerve to be stimulated.

As shown in FIGS. 6-10, the lead 6, according to various embodiments of the present invention, includes a plurality of electrodes 52 located on the distal portion 50. The electrodes 52 can be located on one or more spirals 64 or 76, the generally straight portion 80 or a combination thereof. The electrodes 52 can be aligned in parallel with the nerve to be stimulated. According to a further embodiment of the present invention, the electrodes 52 are located on parallel planes to one another. The parallel planes are orthogonal to the nerve to be stimulated.

Multiple electrodes allow flexibility in the intravascular placement of the distal portion 50 of the lead 6. Not all of the electrodes 52 need to be orientated towards the adjacent nerve or muscle tissue in order for maximum stimulation across the vessel wall to occur. Likewise, the circular or elliptical cross section of the spiral 64 allows the spiral 64 to be rotated within the vessel so as to ensure that at least one electrode is capable of delivering sufficient electrical stimulating pulse across the vessel wall. Additionally, the electrodes can be connected to multiple individual conductors through the lead body allowing for them to be individually addressable. According to this embodiment, the electrodes are adapted to be selected such that the direction of stimulation can be controlled. Stimulation can occur between individual electrodes 52 located on the same spiral 64, different spirals 76 and/or the straight portion 80 providing for greater control over the current field and the direction of stimulation as well as allowing for multiple options for stimulation and sensing.

The electrodes 52 can have any electrode configuration as is known in the art. According to one embodiment of the present invention, at least one electrode 52 can be a ring electrode. According to another embodiment, at least one electrode 52 is a partial ring electrode. According to yet another embodiment of the present invention, the electrodes include an exposed electrode portion and an insulated electrode portion. According to this embodiment, the electrode(s) 52 are masked or otherwise insulated on the inner circumference of the spiral 64 or 76. The exposed electrode portion is located on the outer circumference of the spiral 64 or 76. Exemplary electrodes of this type are described in co-pending published application US 2008/0183264 entitled "Electrode Configurations for Transvascular Nerve Stimulation," which is herein incorporated by reference. The lead body 42 is rotated such that the exposed electrode portion is oriented towards the adjacent nerve, muscle or tissue to be stimulated. The exposed electrode portion is configured such that it is adapted to direct or focus current density towards the stimulation target. The insulated electrode portion is located on the lead body 42 opposite the exposed electrode surface. The insulated electrode portion acts as a shield from the undesired stimulation of an adjacent or nearby nerve or muscle that is not the stimulation target.

The lead 6 can be further stabilized in the internal jugular vein 34 by using a suture in a distal region of the lead body 42. In one embodiment, the lead 6 is further stabilized through the wearing of a neck brace by the patient for a period of time after implantation of the distal portion 50 of the lead 6 in the internal jugular vein. In an alternative embodiment, the lead 6 can include fixation features well known in the art, such as silicone tines or a corkscrew-shaped fixation feature (not shown) at the distal region, to stabilize the lead 6 in the internal jugular vein 34. In other embodiments, the fixation feature can be located at a distal end of the lead 6. The lead 6 can also include an area on the lead body 42 that promotes tissue in-growth. In one embodiment, the area includes a roughened polymer surface on the lead body. In alternative embodiments, the area includes a region of stepped or inset diameter within the lead body 42, within an electrode, or between the lead body 42 and an electrode. In other embodiments, the area includes a polymer mesh, for example, a Dacron mesh, a metal mesh, for example, a stainless steel or nitinol mesh, or a bio-absorbable mesh. Examples of a bio-absorbable mesh include polyglycolic acid, poly-lactic acid, and polydioxanone. The lead 6 can include any combination of sutures, fixation devices, tissue in-growth areas, or a neck brace to improve its stability within the internal jugular vein 34.

The lead 6, according to various embodiments of the present invention, can be delivered to a stimulation site within a vessel adjacent a nerve, muscle, or tissue to be stimulated using standard techniques. According to another embodiment of the present invention, the lead 6 can be inserted in a patient's vasculature system via percutaneous stick directly into a patient's internal jugular vein to deliver therapy to the vagus nerve. According to another embodiment of the present invention, the distal portion 50 of the lead 6 is collapsed and delivered to a stimulation site using a guide catheter. Once the site has been reached and the guide catheter is removed, the spiral located at the distal portion 50 of the lead 6 expands to contact and frictionally engage the vessel walls of the vessel in which it is deployed. Likewise, a stylet or one or more guide wires may be inserted into the lead lumen to straighten the distal portion 50 from its predetermined shape. The distal portion is then guided through the vasculature to a stimulation site located within a vessel. Once a stimulation site has been reached, the guide wire or stylet is removed allowing the distal portion 50 of the lead 6 to return to its predetermined shape, typically a spiral. The distal portion 50 then expands to contact and frictionally engage the vessel walls of the vessel in which it is deployed. The spiral 64 can be rotated within the vessel to orient the electrode(s) 52 towards the stimulation target. Additionally, the lead body 42 can be further rotated or positioned until a maximum or optimum electrical stimulation by the electrode(s) 52 has been achieved across the vessel wall to the adjacent nerve or muscle to be stimulated. The stimulating pulse delivered by the electrode(s) can be measured using an external or an internal device. Additionally, the lead can be repositioned within the vessel by either rotating the lead body 42 within the vessel or reintroducing the guiding member such as the guide catheter or guide wire to straighten the distal portion 50 of the lead 6. The lead 6 can then either be repositioned and/or removed from the vessel. According to a further embodiment of the present invention, the distal portion can be partially deployed from a guide catheter in order to acutely stimulate the electrodes. Once a suitable stimulation site has been identified, the guide catheter can be retracted and the distal portion 50 fully deployed within the vessel at the stimulation site.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead for stimulating a vagus nerve, wherein the lead is adapted to be delivered to a stimulation site within an internal jugular vein having a vessel wall adjacent to the vagus nerve, the lead comprising;

a proximal end adapted to be connected to a pulse generator;

a lead body including a distal portion comprising a first continuous spiral, a second continuous spiral, and a generally straight portion occurring between the first spiral and the second spiral, wherein the first and second spirals are adapted to transition between a collapsed configuration and an expanded configuration sized and shaped for securing and stabilizing the lead at the stimulation site in the internal jugular vein, and wherein in the expanded configuration the spirals are generally aligned with one another and have a predetermined effective outer diameter ranging from about 5 to about 50% greater than an inner diameter of the internal jugular vein such that the spirals are adapted to impart a lateral force on the vessel wall to urge the vessel wall in an outward direction towards the vagus nerve and wherein the generally straight portion is configured to extend generally parallel to a longitudinal axis of the lead body and to the vagus nerve when the lead is implanted in the internal jugular vein;

one or more conductors extending within the lead body including the distal portion; and one or more electrodes adapted to deliver an electrical pulse transvascularly to the nerve to be stimulated located on the distal portion and operatively coupled to the one or more conductors, each of the one or more electrodes comprising a masked portion and an unmasked portion, wherein when the distal portion is in the expanded configuration, the unmasked portion of at least one electrode is located on an outer circumference of the first spiral or the second spiral such that the unmasked portion of the at least one electrode is adapted to be oriented in a direction towards the vagus nerve and to be placed in contact with the vessel wall adjacent to the vagus nerve and the masked portion is located on an inner circumference of the spiral and is adapted to be oriented away from the vagus nerve.

2. The medical electrical lead according to claim 1, wherein a distance between the electrode and the vagus nerve is less than 2 mm.

3. The medical electrical lead according to claim 1, wherein the first spiral winds in a first direction and the second spiral winds in an opposite second direction.

4. The medical electrical lead according to claim 1, wherein the distal portion is sized and shaped so that the unmasked portions of at least two electrodes are located on the outer circumference of the first spiral and/or the second spiral and oriented in a direction towards the vagus nerve when the distal portion is in the expanded configuration.

5. The medical electrical lead according to claim 1, wherein the distal portion comprises a superelastic material selected from the group consisting of Nitinol and MP35N.

6. The medical electrical lead according to claim 1, further comprising at least one electrode located on the generally straight portion.

7. The medial electrical lead according to claim 1, wherein the distal portion comprises one or more electrodes in parallel alignment with the nerve to be stimulated when the lead is implanted.

* * * * *